US009678036B2

(12) United States Patent
Balandin

(10) Patent No.: US 9,678,036 B2
(45) Date of Patent: Jun. 13, 2017

(54) GRAPHENE-BASED GAS AND BIO SENSOR WITH HIGH SENSITIVITY AND SELECTIVITY

(71) Applicant: The Regents of the University of California, Oakland, CA (US)

(72) Inventor: Alexander A. Balandin, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 170 days.

(21) Appl. No.: 14/209,620

(22) Filed: Mar. 13, 2014

(65) Prior Publication Data

US 2014/0260547 A1    Sep. 18, 2014

Related U.S. Application Data

(60) Provisional application No. 61/798,684, filed on Mar. 15, 2013.

(51) Int. Cl.
| | | |
|---|---|---|
| G01N 7/00 | (2006.01) | |
| G01N 9/00 | (2006.01) | |
| G01N 27/414 | (2006.01) | |
| B82Y 15/00 | (2011.01) | |

(52) U.S. Cl.
CPC ........... G01N 27/414 (2013.01); B82Y 15/00 (2013.01)

(58) Field of Classification Search
None
See application file for complete search history.

(56) References Cited

U.S. PATENT DOCUMENTS

| 8,642,996 B2 * | 2/2014 | Cohen ............... B82Y 10/00 257/27 |
| 9,029,228 B2 * | 5/2015 | Seacrist ............ H01L 21/02458 257/643 |
| 9,177,688 B2 * | 11/2015 | Bol ..................... H01L 51/0048 |

(Continued)

OTHER PUBLICATIONS

Novoselov, K. S. et al.,"Two-dimensional gas of massless Dirac fermions in graphene" Nature Publishing Group, vol. 438, Nov. 10, 2005, pp. 197-200.

(Continued)

*Primary Examiner* — Peter Macchiarolo
*Assistant Examiner* — Jermaine Jenkins
(74) *Attorney, Agent, or Firm* — Buchanan Ingersoll & Rooney PC

(57) ABSTRACT

A graphene sensor and method for selective sensing of vapors, gases and biological agents are disclosed. The graphene sensor can include a substrate; a dielectric substrate on an upper layer of the substrate; a layer of graphene on an upper layer of the dielectric substrate; and a source and drain contact on an upper surface of the layer of graphene. The method for detection of vapors, gases and biological objects with low frequency input as a sensing parameter can include exposing a graphene device to at least one vapor, gas, and/or biological object, the graphene device comprising: a substrate; a dielectric substrate on an upper layer of the substrate, a layer of graphene on an upper layer of the dielectric substrate, and a source and drain contact on an upper surface of the layer of graphene; and measuring a change in a noise spectra of the graphene device.

20 Claims, 10 Drawing Sheets

(56) References Cited

U.S. PATENT DOCUMENTS

| | | | | |
|---|---|---|---|---|
| 2012/0058350 | A1* | 3/2012 | Long | B82Y 10/00 428/446 |
| 2013/0113081 | A1* | 5/2013 | Chen | B82Y 10/00 257/602 |
| 2014/0166487 | A1* | 6/2014 | Lieber | G01N 33/48721 204/603 |
| 2014/0260546 | A1* | 9/2014 | Chen | G01N 27/128 73/31.06 |
| 2015/0104046 | A1* | 4/2015 | Norris | H04R 19/005 381/150 |

OTHER PUBLICATIONS

Zhang Y. et al.,"Experimental observation of the quantum Hall effect and Berry's phase in graphene" Nature Publishing Group, vol. 438, Nov. 10, 2005, pp. 201-204.
Blake P. et al.,"Influence of metal contacts and charge inhomogeneity on transport properties of graphene near the neutrality point" Solid State Communications, vol. 149, 2009, pp. 1068-1071.
Geim A. K. et al.,"The rise of graphene" Nature Publishing Group, vol. 6, 2007, pp. 183-191.
Balandin A. A. et al.,"Superior Thermal Conductivity of Single-Layer Graphene" Nano Letters, vol. 8, No. 3, 2008, pp. 902-907.
Balandin A. A."Thermal properties of graphene and nanostructured carbon materials" Nature Materials, Macmillan Publishers Limited, vol. 10, 2011, pp. 569-581.
Meric I. et al.,"Current saturation in zero-bandgap, top-gated graphene field-effect transistors" Letters, Nature nanotechnology, vol. 3, Nov. 2008, pp. 654-659.
Liao L. et a.,"High-speed graphene transistors with a self-aligned nanowire gate" Nature, vol. 467, Sep. 16, 2010, pp. 305-308.
Ryzhii V. et al.,"Graphene bilayer field-effect phototransistor for terahertz and infrared detection" Physical Review B, vol. 79, pp. 24531-1-245311-8, 2009.
Yang X. et al.,"Graphene Ambipolar Multiplier Phase Detector" IEEE Electron Device Letters, vol. 32, No. 10, Oct. 2011, pp. 1328-1330.
Kim K. S. et al.,"Large-scale pattern growth of graphene films for stretchable transparent electrodes" Nature, vol. 457, Feb. 5, 2009, pp. 706-710.
Li X. et al."Large-Area Synthesis of High-Quality and Uniform Graphene Films on Copper Foils" Science, vol. 324, Jun. 5, 2009, 4 pages.
Hernandez Y. et al.,"High-yield production of graphene by liquid-phase exfoliation of graphite" Nature nanotechnology, vol. 3, Sep. 2008, pp. 563-568.
Amini S. et al."Growth of large-area graphene films from metal-carbon melts" Journal of Applied Physics, vol. 108, 2010, 8 pages.
Nolen C. M. et al.,"High-Throughput Large-Area Automated Identification and Quality Control of Graphene and Few-Layer Graphene Films" ACS Nano, vol. 5, 2011, No. 2, pp. 914-922.
Schedin F. et al.,"Detection of individual gas molecules adsorbed on graphene" Nature Materials, vol. 6, Sep. 2007, pp. 652-655.
Rumyantsev S. et al.,"Electrical and noise characteristics of graphene field-effect transistors: ambient effects, noise sources and physical mechanisms" Journal of Physics: Condensed Matter, vol. 22, 2010, 8 pages.
Rumyantsev S. et al.,"Low-frequency noise in graphene field-effect transistors" 21st International Conference on Noise and Fluctuations (ICNF), 2011, pp. 234-237.
Xia F. et al.,"The origins and limits of metal—graphene junction resistance" Nature Nanotechnology, vol. 6, Mar. 2011, pp. 179-184.
Russo S. et al.,"Contact resistanceingraphene-baseddevices" Physica, vol. 42, 2010, pp. 677-679.
Ratinac K. R. et al.,"Toward Ubiquitous Environmental Gas SensorssCapitalizing on the Promise of Graphene" Environ. Sci. Technol. vol. 44, 2010, pp. 1167-1176.

Potyrailo R. A. et al.,"Materials and Transducers Toward Selective Wireless Gas Sensing" Chemical Reviews, vol. 111, 2011, pp. 7315-7354.
Jensen K. et al.,"An atomic-resolution nanomechanical mass sensor" Nature nanotechnology, vol. 3, Sep. 2008, pp. 533-537.
Johnson A. T. C. et al.,"DNA-decorated carbon nanotubes for chemical sensing" Semiconductor Science and Technology, vol. 21, 2006, 6 pages.
Stall C. et al.,"DNA-Decorated Carbon Nanotubes for Chemical Sensing" Nano Letters, vol. 5, No. 9, 2005, pp. 1774-1778.
Dua V. et al.,"All-Organic Vapor Sensor Using Inkjet-Printed Reduced Graphene Oxide" Angew. Chem. Int. Ed., vol. 49, 2010, pp. 1-5.
Yu K. et al.,"Growth of carbon nanowalls at atmospheric pressure for one-step gas sensor fabrication" Nanoscale Research Letters, vol. 6, 2011, 9 pages.
Cui Y. et al.,"Chemical Functionalization of Graphene Enabled by Phage Displayed Peptides" Nano Letters, vol. 10, 2010, pp. 4559-4565.
Lu Y. et al.,"DNA-decorated graphene chemical sensors" Applied Physics Letters, vol. 97, 2010, 4 pages.
Ratinac K. et al.,"Toward Ubiquitous Environmental Gas SensorssCapitalizing on the Promise of Graphene" Environ. Sci. Technol., vol. 44, No. 4, 2010, pp. 1167-1176.
Kauffman D. R. et al.,"Graphene versus carbon nanotubes for chemical sensor and fuel cell applications" Analyst, vol. 135, No. 11, Nov. 2010, pp. 2745-3012.
Jiang H.,"Chemical Preparation of Graphene-Based Nanomaterials and Their Applications in Chemical and Biological Sensors" Small, vol. 7, No. 17, 2011, pp. 2413-2427.
Hill E. W. et al.,"Graphene Sensors" IEEE Sensors Journal, vol. 11, No. 12, Dec. 2011, pp. 3161-3170.
Bruschi P. et al.,"Gas and vapour effects on the resistance fluctuation spectra of conducting polymer thin-film resistors" Sensors and Actuators B, vol. 18-19, 1994, pp. 421-425.
Kish L. B. et al.,"Extracting information from noise spectra of chemical sensors: single sensor electronic noses and tongues" Sensors and Actuators B, vol. 71, 2000, pp. 55-59.
Aroutiounian V. M. et al.,"Noise Spectroscopy of Gas Sensors" IEEE Sensors Journal, vol. 8, No. 6, Jun. 2008, pp. 786-790.
Calizo I. et al.,"Variable temperature Raman microscopy as a nanometrology tool for graphene layers and graphene-based devices" Applied Physics Letters, vol. 91, 2007, 4 pages.
Calizo I. et al.,"Ultraviolet Raman microscopy of single and multilayer graphene" Journal of Applied Physics, vol. 106, 2009, 6 pages.
Shao Q. et al.,"Flicker Noise in Bilayer Graphene Transistors" IEEE Electron Device Letters, vol. 30, No. 3, Mar. 2009, pp. 288-290.
Liu G. et al.,"Low-frequency electronic noise in the double-gate single-layer graphene transistors" Applied Physics Letters, vol. 95, 2009, 4 pages.
Liu, G.,"Low-Frequency Electronic Noise in Graphene Transistors: Comparison with Carbon Nanotubes" International Journal of High Speed Electronics and Systems, vol. 20, No. 1, 2011, pp. 161-170.
Imam S. A. et al.,"Low-frequency noise and hysteresis in graphene field-effect transistors on oxide" Micro & Nano Letters, vol. 5, Iss. 1, 2010, pp. 37-41.
Lee Y. G. et al.,"Fast transient charging at the graphene/ $SiO_2$ interface causing hysteretic device characteristics" Applied Physics Letters, vol. 98, 2011, 4 pages.
Ueda T. et al.,"Development of carbon nanotube-based gas sensors for NOx gas detection working at low temperature" Physica E, vol. 40, 2008, pp. 2272-2277.
Ko G. et al.,"Graphene-based nitrogen dioxide gas sensors" Current Applied Physics, vol. 10, 2010, pp. 1002-1004.
Levinshtein M. E. et al.,"Noise spectroscopy of local levels in 1 semiconductors" Semicond. Sci. Technol., vol. 9, 1994, pages.
Galperin Y. M. et al.,"Disorder-Induced Low-Frequency Noise in Small Systems: Point and Tunnel Contacts in the Normal and Superconducting State" Europhysics Letters, Eurqvhys. Lett., vol. 10, No. 8, 1989, 7 pages.
Lukyanchikova N. B.,"Sources of the Lorentzian Components in the Low-Frequency Noise Spectra of Submicron Metal-Oxide-

(56) References Cited

OTHER PUBLICATIONS

Semiconductor Field-Effect Transistors" American Scientific Publishers (Chapter 10), 2002, pp. 201-233.
Mitin V., "Generation-Recombination Noise in Semiconductors" American Scientific Publishers (Chapter 2), 2002, pp. 11-29.

* cited by examiner

GRAPHENE-BASED GAS AND BIO SENSOR WITH HIGH SENSITIVITY AND SELECTIVITY

RELATED APPLICATION(S)

The present application claims priority under 35 U.S.C. 119 to U.S. Provisional Patent Application No. 61/798,684, filed on Mar. 15, 2013, the entire content of which is hereby incorporated by reference.

FIELD

This invention relates to the sensors and detectors for vapors, gases and biological objects (DNA, viruses and bacteria) implemented with graphene, and more particularly to a method of sensing vapors, gases and biological objects, which allows selective detection without a graphene surface functionalization.

BACKGROUND INFORMATION

Graphene is a planar sheet of carbon atoms arranged in honeycomb lattice, which has attracted attention owing to its extremely high mobility, thermal conductivity, and strongly tunable electrical conduction, which can be controlled with the gate bias. Device applications of graphene for high frequency, analog, mixed signal communication and THz generation have been proposed. For example, graphene chemical vapor deposition (CVD) growth and other synthesis techniques together with development of the large-scale quality control methods for graphene can make practical applications of graphene feasible.

Graphene, with its extremely high surface-to-volume ratio, can become a natural choice material for sensor applications. The single-molecule sensitivity of graphene devices has been demonstrated at the early stages of graphene research. For example, it has been suggested that the exceptional surface-to-volume ratio, high electrical conductivity, low thermal and 1/f noise, relatively low contact resistance, and ability to strongly tune the conductivity by the gate in graphene transistors may make them promising for gas sensing applications. Graphene resistivity, frequency of the surface acoustic waves (SAW), Hall resistivity, and the shift of the Dirac voltage has been used as sensing parameters. For example, the sensitivity of graphene devices to $NH_3$, $NO_2$, $CO$, $CO_2$, $O_2$, has been demonstrated. The high-gas sensitivity of graphene, which leads to its ability to detect ultra-low concentrations (down to less than 1 ppb) of different gases, and the linear dependence of the response to the gas concentration have been disclosed in several publication.

However, the selectivity of the graphene-based gas sensors is much less explored for the sensors utilizing all the above-mentioned sensing parameters. In accordance with an exemplary embodiment, the low-frequency noise can be used as the sensing parameter to enhance selectivity is demonstrated. For example, while the electrical resistivity or other DC parameter can serve as a quantitative parameter to measure the gas concentration, the low-frequency noise can help to discriminate between individual gases.

SUMMARY

In accordance with an exemplary embodiment, a graphene sensor for selective sensing of vapors, gases and biological agents is disclosed, the graphene sensor comprising: a substrate; a dielectric substrate on an upper layer of the substrate; a layer of graphene on an upper layer of the dielectric substrate; and a source and drain contact on an upper surface of the layer of graphene.

In accordance with an exemplary embodiment, a graphene sensor for selective sensing of vapors, gases and biological agents is disclosed, the graphene sensor comprising: a substrate; a dielectric substrate on an upper layer of the substrate; one or more ribbons of graphene on an upper layer of the dielectric substrate; and a metal electrode.

In accordance with an exemplary embodiment, a method for selective detection of vapors, gases and biological objects with low frequency input as a sensing parameter using a graphene device is disclosed, the method comprising: exposing the graphene device to at least one vapor, gas, and/or biological object, the graphene device comprising: a substrate; a dielectric substrate on an upper layer of the substrate, a layer of graphene on an upper layer of the dielectric substrate, and a source and drain contact on an upper surface of the layer of graphene; and measuring a change in a noise spectra of the graphene device.

In accordance with an exemplary embodiment, a method for selective detection of vapors, gases and biological objects with low frequency input as a sensing parameter using a graphene device is disclosed, the method comprising: exposing the graphene device to at least one vapor, gas, and/or biological object, the graphene device comprising: a substrate, a dielectric substrate on an upper layer of the substrate, one or more ribbons of graphene on an upper layer of the dielectric substrate, and a metal electrode; and measuring a change in a noise spectra of the graphene device.

BRIEF DESCRIPTION OF THE DRAWINGS

Exemplary embodiments will be disclosed more closely with reference to the accompanying drawings in which.

DETAILED DESCRIPTION

Figure 1:
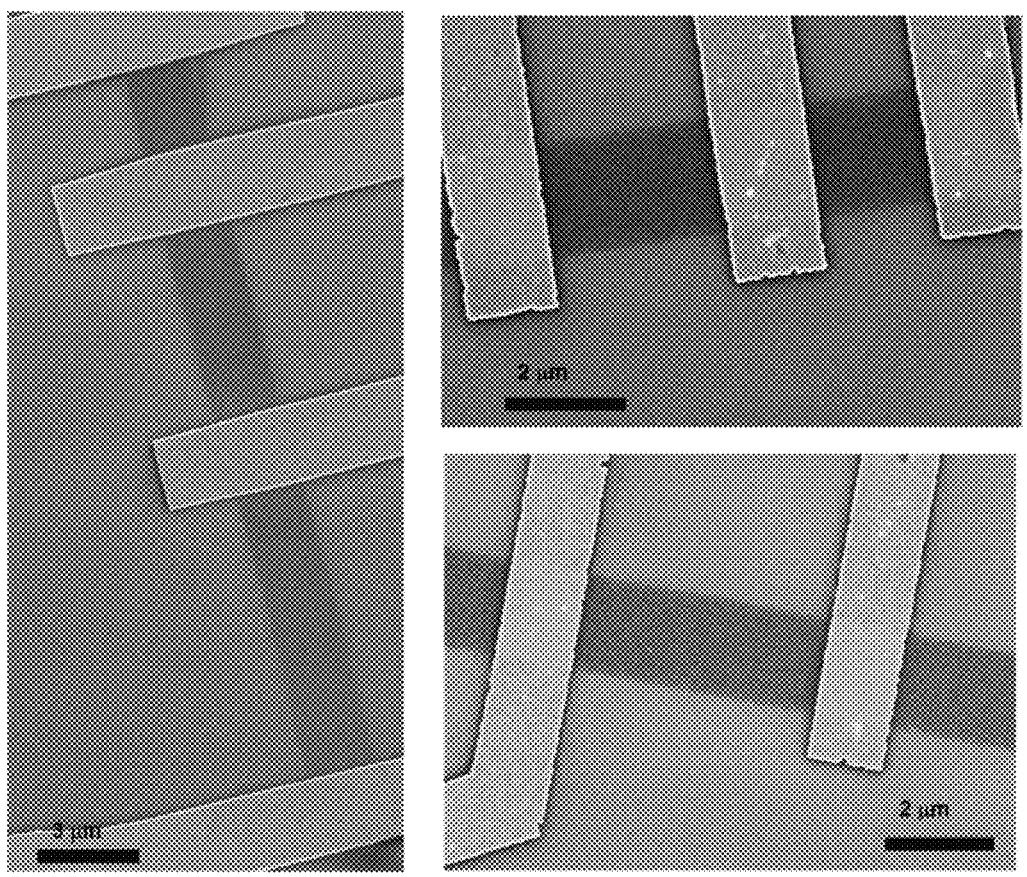
FIG. 1 shows scanning electron microscopy images of back-gated graphene devices.

In accordance with an exemplary embodiment, a device and method for selective detection of gases, vapors, and biological objects with graphene-based devices that do not require surface functionalization is disclosed. The disclosure is based on that vapors of different chemicals produce distinguishably different effects on the low-frequency noise spectra of graphene. Some gases change the electrical resistance of graphene devices without changing their low-frequency noise spectra while other gases modify the noise spectra by induce Lorentzian components with different frequencies, which can be used for selective sensing. The disclosure indicates that the low-frequency noise in combination with other sensing parameters can allow one to achieve the selective sensing of gases, vapors and biological objects such as DNA, viruses, bacteria and related with a single pristine graphene device. In addition, the method of sensing with graphene does not require graphene surface functionalization or fabrication of an array of the devices with each tuned to a certain chemical or biological object.

In accordance with an exemplary embodiment, the similarity of properties between graphene and carbon nanotubes (CNTs), for example, large surface-to-volume ratio, high electron mobility, graphene can be used for sensing a wider range of applications following the CNT analogy. For example, CNTs have been used as nano-mechanical mass sensors with atomic resolution. For example, it has been demonstrated that a versatile class of nanoscale chemical sensors can be developed based on single-stranded DNA (sand) for chemical recognition and CNT field-effect transistors (Fetes) for the electronic read-out. CNT Fetes with sand coating responded to vapors that caused no detectable conductivity change in bare devices. In accordance with an exemplary embodiment, sand-decorated CNTs have been observed, such that the sensor surface can be self-regenerating. In accordance with an exemplary embodiment, for example, the samples can maintain a constant response with no need for sensor refreshing through at least 50 gas exposure cycles.

In accordance with an exemplary embodiment, to improve the gas-response selectivity of graphene and related materials, several graphene preparation and functionalization methods have been developed. For example, reduced graphene oxide (RGO) platelets can be used for vapor sensing. The RGO films can reversibly and selectively detect chemically aggressive vapors such as $NO_2$ or $Cl_2$. The detection can be achieved at room temperature (RT) for vapor concentrations ranging from approximately 100 ppm to 500 ppb. For example, two-dimensional "graphitic" platelets, oriented vertically on a substrate, can respond to relatively low concentrations of $NO_2$ and $NH_3$ gases. Sensing applications of graphene can be enabled via not only chemical but also biological functionalization, including by the use of phage displayed peptides and DNA functionalization.

Sensor sensitivity can be limited by the electronic noise. Therefore, noise can be considered as one of the main limiting factors for the detector operation. However, the electronic noise spectrum itself, can be used as a sensing parameter increasing the sensor sensitivity and selectivity. For example, exposure of a polymer thin-film resistor to different gases and vapors affects not only the resistance of the sensor but also the spectrum of the resistance fluctuations. For example, by using noise as a sensing parameter in combination with the resistance measurements one can increase the sensor selectivity. It is known that not only the amplitude but also the shape of the spectra changes under the gas exposure. In many cases, noise is a more sensitive parameter than the resistance. It has also been found that the changes in the resistance and noise are not always correlated and can be used as independent parameters in the analysis of the sensor response.

A low-frequency noise in graphene transistors may not always be a detrimental phenomenon, which presents problems for its device application. In accordance with an exemplary embodiment, vapors of various chemicals affect the low-frequency noise spectra of graphene devices in distinctively different ways is experimentally disclosed. For example, some vapors change the electrical resistance of graphene devices without changing their noise spectra while others introduce distinctive bulges over the smooth 1/f background. For example, the characteristic frequencies of these bulges can be clearly different for different chemicals.

In accordance with an exemplary embodiment, noise can be used to discriminate between different gases. In combination with other sensing parameters, this approach may allow one to build a selective gas sensor with a single transistor made of pristine graphene, which does not require an array of sensors functionalized for each chemical separately.

In accordance with an exemplary embodiment, a mechanical exfoliation technique from the bulk highly oriented pyrolytic graphite is disclosed. The p-type highly-doped Si wafers covered with 300-nm thermally grown $SiO_2$ can serve as a substrate and back-gate for the graphene device channels. The single layer graphene (SLG) and bilayer graphene (BLG) samples were identified using the micro-Raman spectroscopy via deconvolution of the 2D band and comparison of the G peak and 2D band intensities. The 10-nm Cr/100-nm Au source and drain contacts were deposited on graphene by the electron beam evaporation (EBE). The bars connected graphene to the pre-deposited Cr/Au metal contact pads. FIG. 1 shows scanning electron microscopy (SEM) images of several back-gated graphene transistors fabricated using the described approach.

The low-frequency noise was measured in the common source configuration with a drain load resistor $R_L$=1-10 KΩ in a frequency range from approximately 1 Hz to 50 kHz at room temperature (RT). The voltage-referred electrical current fluctuations $S_V$ from the load resistor $R_L$ connected in series with the drain were analyzed by a SR770 FFT spectrum analyzer. In accordance with an exemplary embodiment, different vapors can be generated by bubbling dry carrier gas (air) through a respective solvent and further diluting the gas flow with the dry carrier gas. In accordance with an exemplary embodiment, all vapors can be generated at concentrations of approximately 0.5 $P/P_o$, where P is the vapor pressure during the experiment and $P_o$ is the saturated vapor pressure. Upon completing the measurements with one vapor and before the exposure to another vapor, each device was kept in vacuum for several hours at room temperature (RT).

Figure 2:
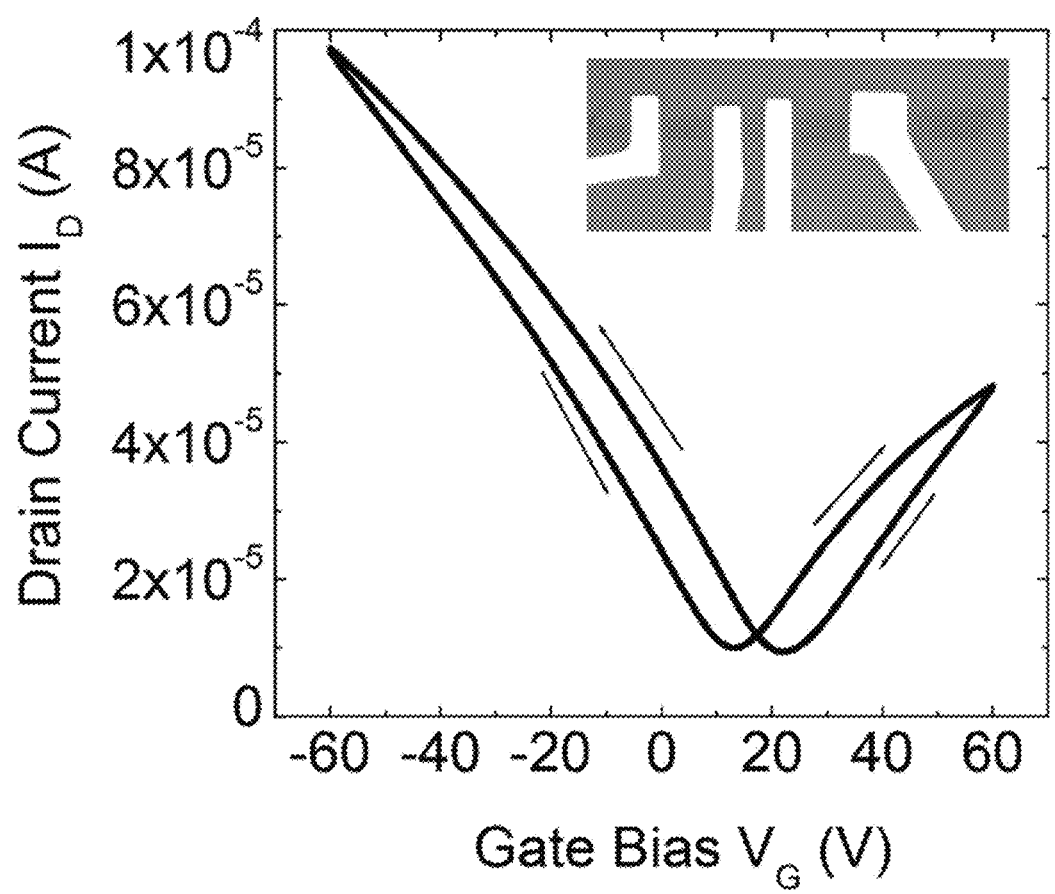
FIG. 2 shows transfer current-voltage characteristic of a typical back-gated graphene transistor used for the gas sensing tests, and wherein the arrows indicate the direction of the gate voltage sweep, and the inset shows an optical microscopy image of the graphene transistor with the top metal electrodes.

FIG. 2 shows current voltage characteristic of a back-gated transistor with the SLG channel measured at ambient conditions. The charge neutrality point, also referred to as Dirac voltage, was about 10-20 V for the as fabricated devices selected for this disclosure. The field-effect and effective mobilities extracted from the current-voltage characteristics were in the range 5000 to 10000 cm$^2$/Vs. In accordance with an exemplary embodiment, all devices revealed the hysteresis under the direct and reverse gate voltage scans. This is a known effect attributed to the slow carrier relaxations due to the presence of deep traps. In accordance with an exemplary embodiment, pulse measurements showed that these relaxation processes were non-exponential within the time scale from about 20 ms to at least 1000 seconds. In order to avoid this unstable behavior, all measurements at zero gate voltage were performed, for example, on the "hole" part of the current voltage characteristic (see FIG. 2).

Figure 3:
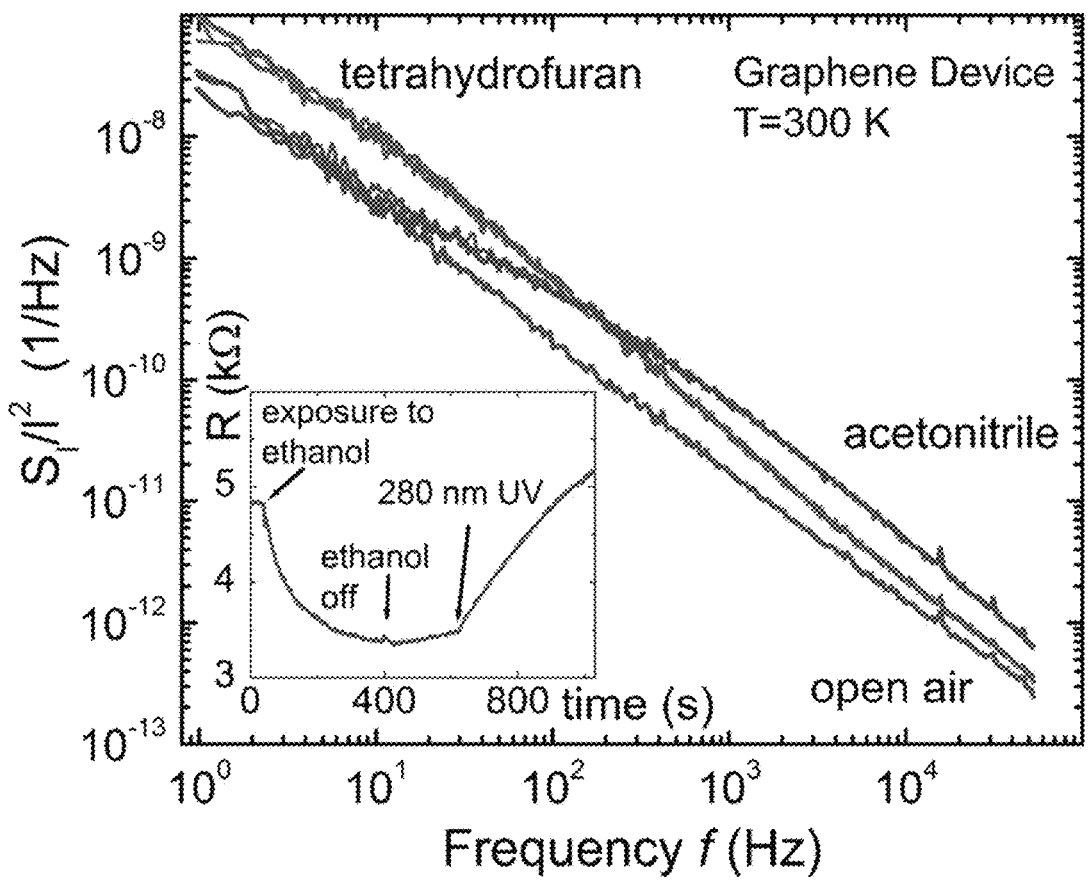
FIG. 3 shows noise spectra of single layer graphene (SLG) transistors measured in open air and under the exposure to acetonitrile and tetrahydrofuran vapors, wherein the gate bias is $V_G=0$ V with the source-drain voltage is $V_D=100$ mV, and the inset shows the resistance response of the graphene transistor to the exposure of ethanol as a function of time, and the gate bias for the data presented in the insert is $V_G=0$ V.

After measuring the transistor current-voltage characteristics the devices were exposed to the laminar flow of individual vapors such as methanol, ethanol, tetrahydrofuran, chloroform, acetonitrile, toluene, and methylene chloride. An inset in FIG. 3 shows an example of the resistance change under the influence of ethanol. As seen, the resistance response is rather slow taking several hundreds of seconds to reach the steady state condition. The process of degassing can be slower but can be accelerated by the exposure to ultraviolet (UV) light. In the inset, one of the arrows shows the moment of time when the 280-nm light-emitting diode (LED) was turned on. The effect of UV cleaning is known for carbon nanotubes and graphene gas sensors. However, extending exposure to UV can irreversibly alter the graphene device characteristics. Therefore, this method of degassing was not used for selective gas sensing experiments.

FIG. 3 shows examples of the noise spectra measured in open air and under the influence of tetrahydrofuran and acetonitrile vapors. The noise was measured in approximately 1 minute after the device exposure to the vapor. The measurements were repeated several times with a time interval of approximately 5 minute. There are two and three overlapping spectra in FIG. 3 for acetonitrile and tetrahydrofuran, respectively, corresponding to multiple measurements indicating excellent reproducibility of the noise measurements. As a result of the vapor exposure the noise increases and the shape of the noise spectra changes. The appearance of characteristic bulges, over 1/f noise background, can indicate a contribution of the random processes with the well-defined relaxation time. For example, in the case of a single relaxation time, the noise spectrum has the form of the Lorentzian:

$$S\alpha \frac{1}{1+(\omega\tau)^2} \quad (1)$$

where $\tau$ is the relaxation time and $\omega=2\pi f$ is the circular frequency.

In semiconductors, for example, this kind of excess noise can be associated with the generation-recombination (G-R) noise, which can be attributed to the fluctuations of the occupancy of the local energy levels. The temperature dependence of the G-R noise in semiconductors allows one to determine all parameters of the given local level, which is the subject of the so-called noise spectroscopy. Other mechanisms also can lead to the Lorentzian type of the spectra. For example, mobility fluctuations with a single relaxation time can also reveal themselves as the Lorentzian bulges. In addition to the Lorentzians observed due to the G-R or mobility fluctuation processes there have been reports of the Lorentzian noise induced by shot or Nyquist noise in MOSFETs. In previous studies of low-frequency noise in graphene devices, it has be found that the number-of-carriers fluctuation mechanism, typically responsible for the GR noise, which does not explain the gate bias dependence of noise in graphene. Accordingly, for this reason, in the present disclosure, the term GR noise was avoided in reference to the observed bulges in the low-frequency spectra of graphene devices exposed to vapors. Here and below, the term Lorentzian noise instead is adopted.

Figure 4:
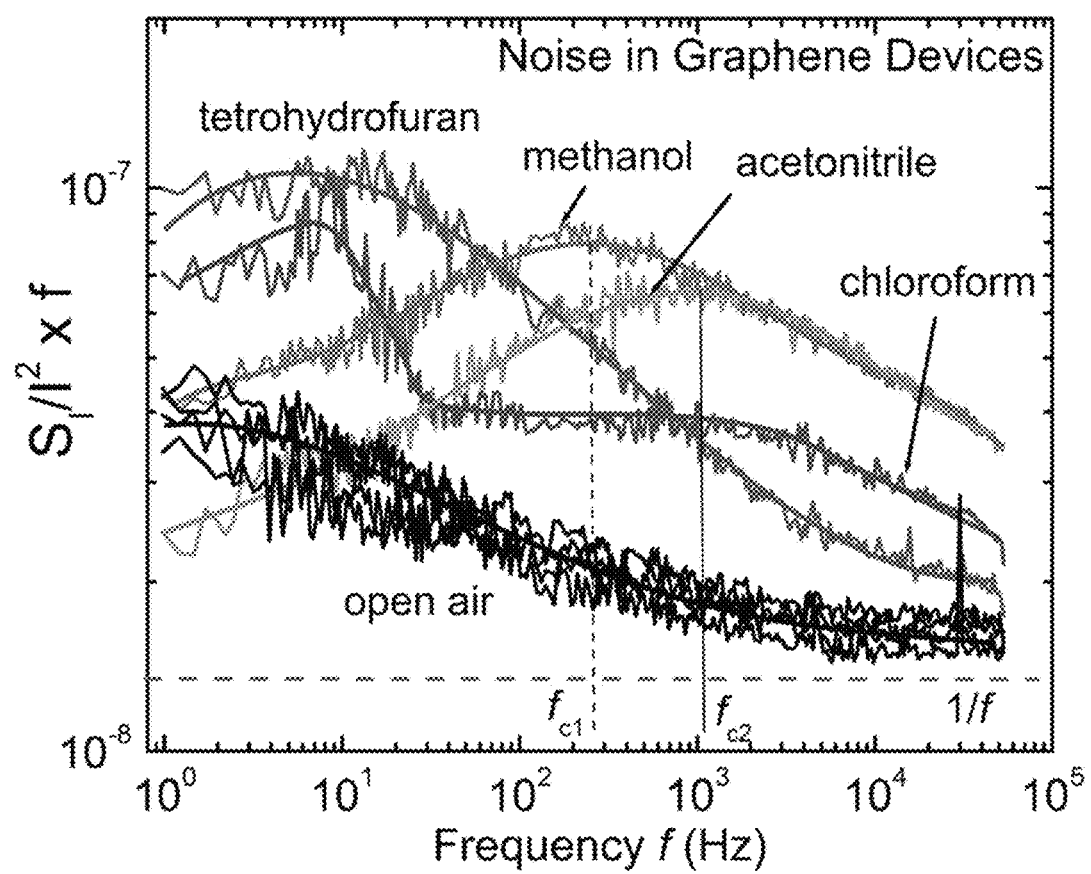
FIG. 4 shows noise spectral density $S_f/I^2$ multiplied by frequency f versus frequency f for the device in open air and under the influence of different vapors, wherein different vapors induce noise with different characteristic frequencies $f_c$ and the frequencies, $f_c$, are shown explicitly for two different gases, the solid lines show the polynomial fitting of the experimental data, and the difference in the frequency $f_c$ is sufficient for reliable identification of different gases with the same graphene transistor, for comparison the pure 1/f noise dependence is also indicated.

In order to establish the characteristic frequency $f_c=\frac{1}{2\pi\tau}$ of the Lorentzian noise for each given vapor, in FIG. 4, the noise spectra multiplied by the frequency f, that is, $s_f/I^2 \times f$, versus f was plotted. As shown, in accordance with an exemplary embodiment, the dependencies can be distinguished maxima at frequencies fc, which are different for different vapors. In accordance with an exemplary embodiment, the results suggest that the frequency $f_c$ can be a distinctive signature of a given vapor. In accordance with an exemplary embodiment, from the physics point of view, there can be two reasons for the Lorentzian noise in graphene appearing under the gas exposure. First, the gas molecules can create specific traps and scattering centers in graphene, which lead to either number of carriers fluctuation due to the fluctuations of traps occupancy or to the mobility fluctuations due to fluctuations of the scattering cross sections. Another scenario is that the kinetic of the molecule adsorption and desorption contributes to noise. The characteristic time scale for the adsorption of vapors was several hundreds of seconds. For example, in accordance with an exemplary embodiment, it is even longer for the degassing. This corresponds to much lower characteristic frequencies than those observe in the present disclosure. Therefore, in accordance with an exemplary embodiment, the appearance of the Lorentzian noise can be related to the charge traps created as a result of vapor exposure. However, the specific mechanism of the observed Lorentzian noise in graphene can be different from that in semiconductor devices.

Table 1 presents the characteristic frequencies $f_c$ and the relative resistance $\Delta R/R$ changes in graphene devices for different vapors (R is the resistance). In accordance with an exemplary embodiment, despite of the large resistance changes under exposure to toluene and methylene chloride the noise spectra did not alter under exposure to these vapors. For example, as shown in Table 1, a combination of the resistance change and frequency $f_c$ provides a unique characteristic for identification of the tested chemicals. In accordance with an exemplary embodiment, the data summarized in Table 1 can be used for the selective gas sensing using a single graphene transistor. For example, the latter is a major positive factor for sensor technology since it allows one to avoid fabrication of a dense array of sensors functionalized for individual gases.

TABLE 1

| Frequency $f_c$ and $\Delta R/R$ in Graphene for Different Vapors | | |
|---|---|---|
| Vapor | $f_c$ (Hz) | $\Delta R/R$ % |
| Ethanol | 400-500 | −50 |
| Methanol | 250-400 | −40 |
| Tetrahydrofuran | 10-20 | +18 |
| Chloroform | 7-9 and 1300-1600 | −25 |
| Acetonitrile | 500-700 | −35 |
| Toluene | NA | +15 |
| Methylene Chloride | NA | −48 |

Figure 5:
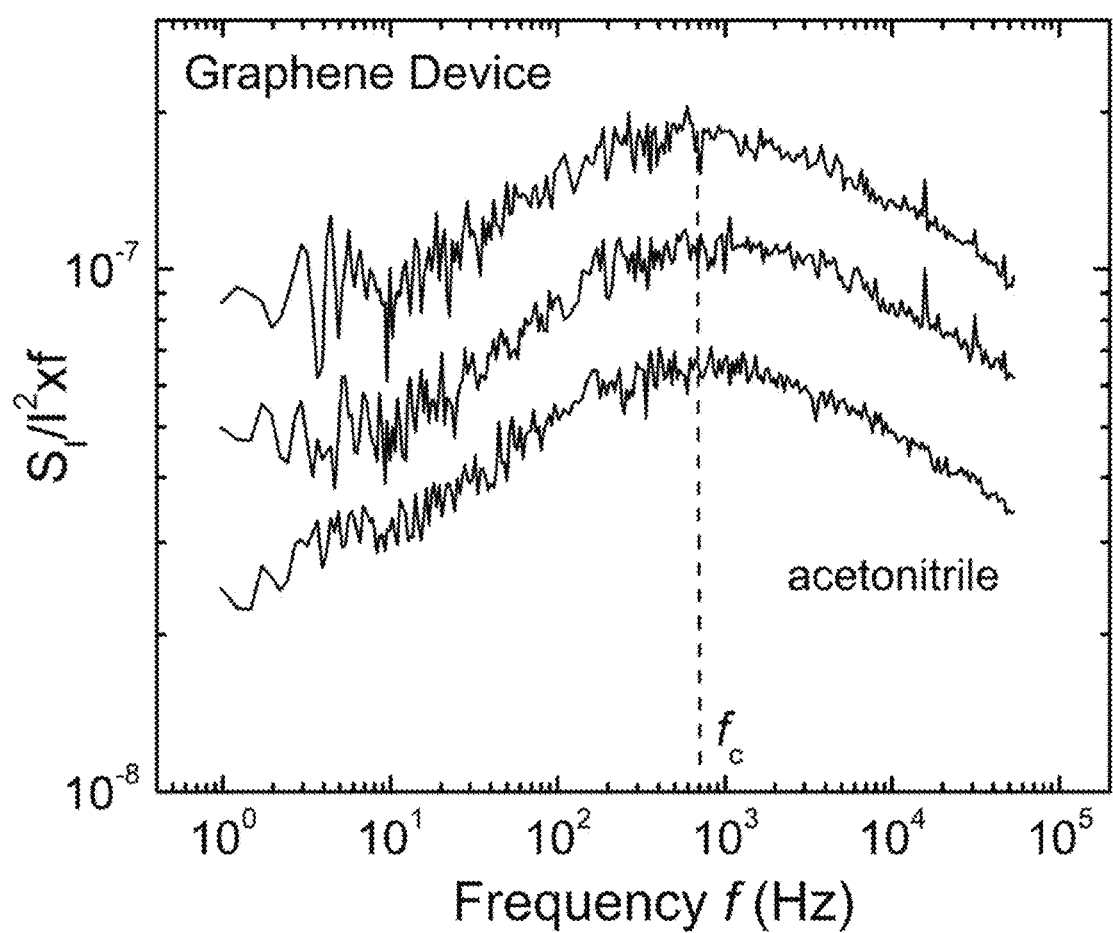
FIG. 5 shows noise spectral density $S_f/I^2$ multiplied by frequency f versus frequency f for three different single-layer-graphene transistors exposed to acetonitrile vapor, and wherein the excellent reproducibility of the noise response of the graphene devices showing the same frequency $f_c$ for all three devices is shown.

In accordance with an exemplary embodiment, a selected set of chemicals vapors on different graphene device samples were tested and alternated different vapors for the same samples. In accordance with an exemplary embodiment, it was found that the results were well reproducible provided that the graphene transistors were degassed by keeping in vacuum at room temperature (RT) for at least 2-3 hours prior the measurements. FIG. 5 shows $S_f/I^2 \times f$ versus frequency $f_c$ dependencies for three different graphene transistors under exposure to the acetonitrile vapor. As shown in FIG. 5, despite different amplitude of the noise the frequency $f_c$ is the same for all three devices.

Figure 6:
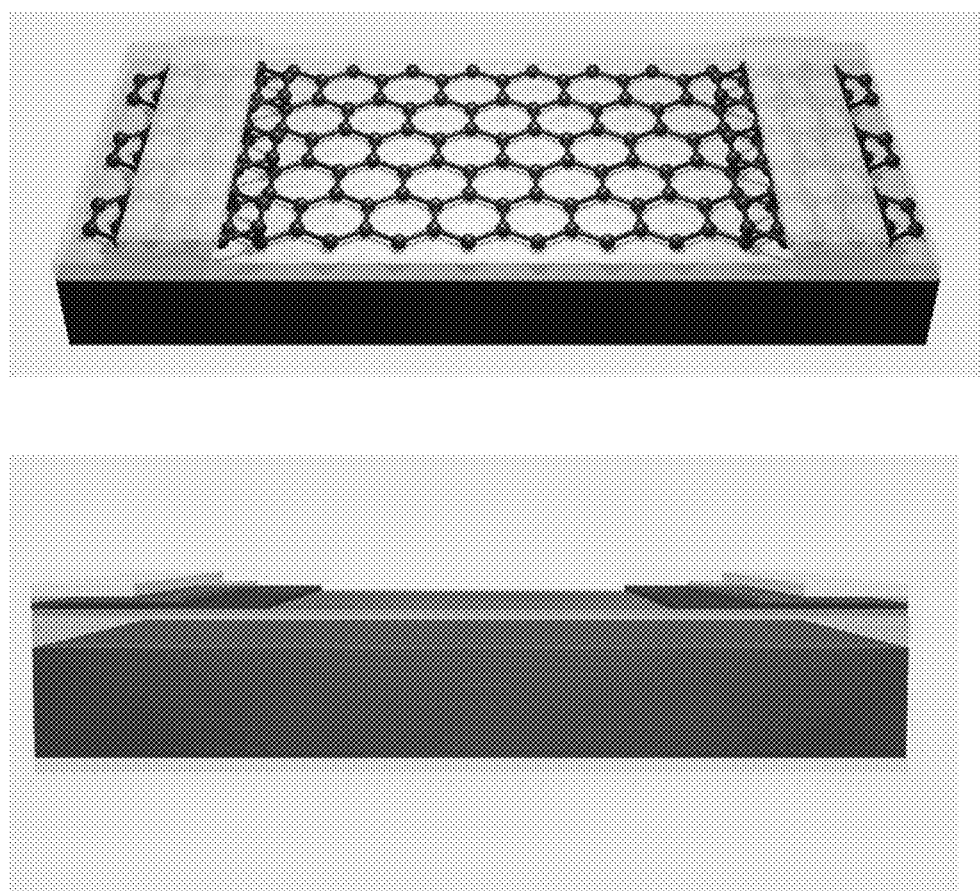
FIG. 6 shows schematic of a top view and a side view of the graphene sensor.

FIG. 6 shows schematic of a top view and a side view of the graphene sensor. As shown in FIG. 6, the graphene sensor for selective sensing of vapors, gases and biological agents, can include, for example, a substrate; a dielectric substrate on an upper layer of the substrate; a layer of graphene on an upper layer of the dielectric substrate; and a source and drain contact on an upper surface of the layer of graphene, or alternatively, the graphene sensor for selective sensing of vapors, gases and biological agents, can include a substrate; a dielectric substrate on an upper layer of the substrate; one or more ribbons of graphene on an upper layer of the dielectric substrate; and a metal electrode.

Figure 7:
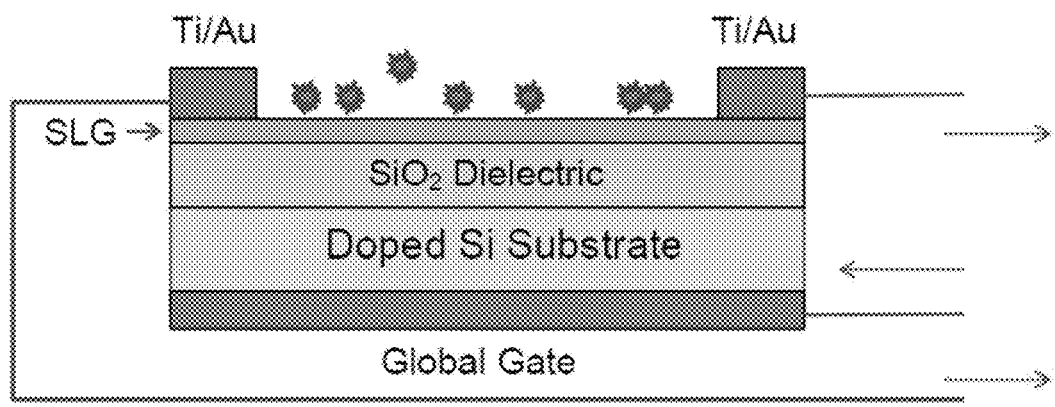
FIG. 7 shows a schematic of the operation principle of the graphene sensor for vapor, gas and biological agents showing the biasing scheme (top panel) and electrical circuit for the low-frequency noise spectrum input, used as an additional sensing parameter (bottom panel).
Figure 7:
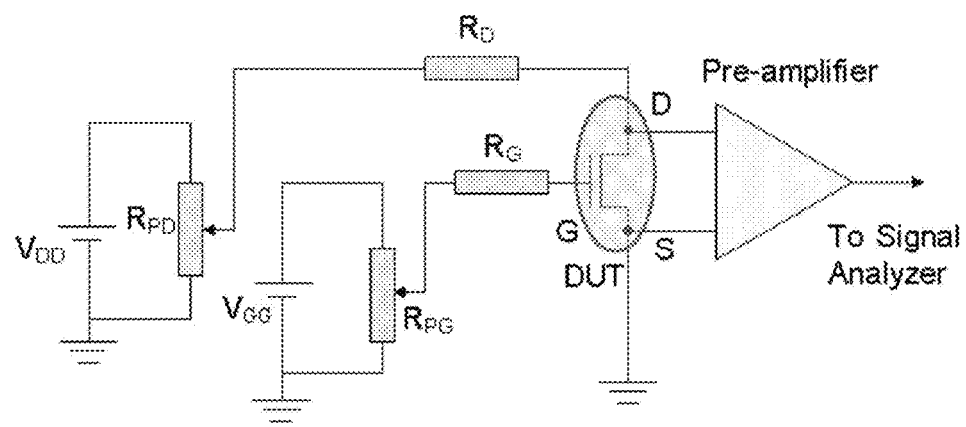

FIG. 7 shows schematic of the operation principle of the graphene sensor for vapor, gas and biological agents showing the biasing scheme (top panel) and electrical circuit for the low-frequency noise spectrum input, used as an additional sensing parameter (bottom panel). In accordance with an exemplary embodiment, the low-frequency noise can be measured in the linear region of the source-drain bias keeping the source at ground potential. Several rechargeable lead-acid batteries connected together in series can be used to provide the drain and gate biases through the resistive voltage-divider network. In accordance with an exemplary embodiment, the metal film resistors for $R_D$ and $R_G$ can be selected because of their very low 1/f noise characteristics. The resistors $R_{PD}$ and $R_{PG}$ can be wire-wound potentiometers to vary the potentials at the terminals. The graphene sensor (indicated in the schematics as DUT) source-drain resistance can be a function of the gate potential. The appropriate choice of the $R_D$, which is approximately 10 times higher than the graphene sensor resistance and $R_D \ll R_{PG}$, helped us to minimize the thermal noise contributions from the external circuits. The whole setup can be placed inside the metal shielding box to reduce the effects of environmental noises and electromagnetic fields. The pre-amplifier can be powered by the low-noise DC battery during the noise data collection to minimize the 60 Hz power line frequency contribution to the noise data. The current fluctuations referenced to the source-drain voltage can be measured in the following way: First, the fluctuations can be amplified with a low-noise preamplifier with a voltage gain ranging from 100 to 1000. The amplifier input can be AC coupled to avoid the DC offset. The low- and high-pass filters of the preamplifier can be chosen to pass frequencies from 0.03 Hz to 100 KHz. Second, the amplified fluctuating signals can be fed to the dynamic signal analyzer to measure the noise power spectrum. The noise data were averaged 50 times. The background noise, which was measured at zero drain bias, was subtracted from the data set. Finally, the noise data was corrected for the amplifier gain and translate to the voltage noise power.

Figure 8:
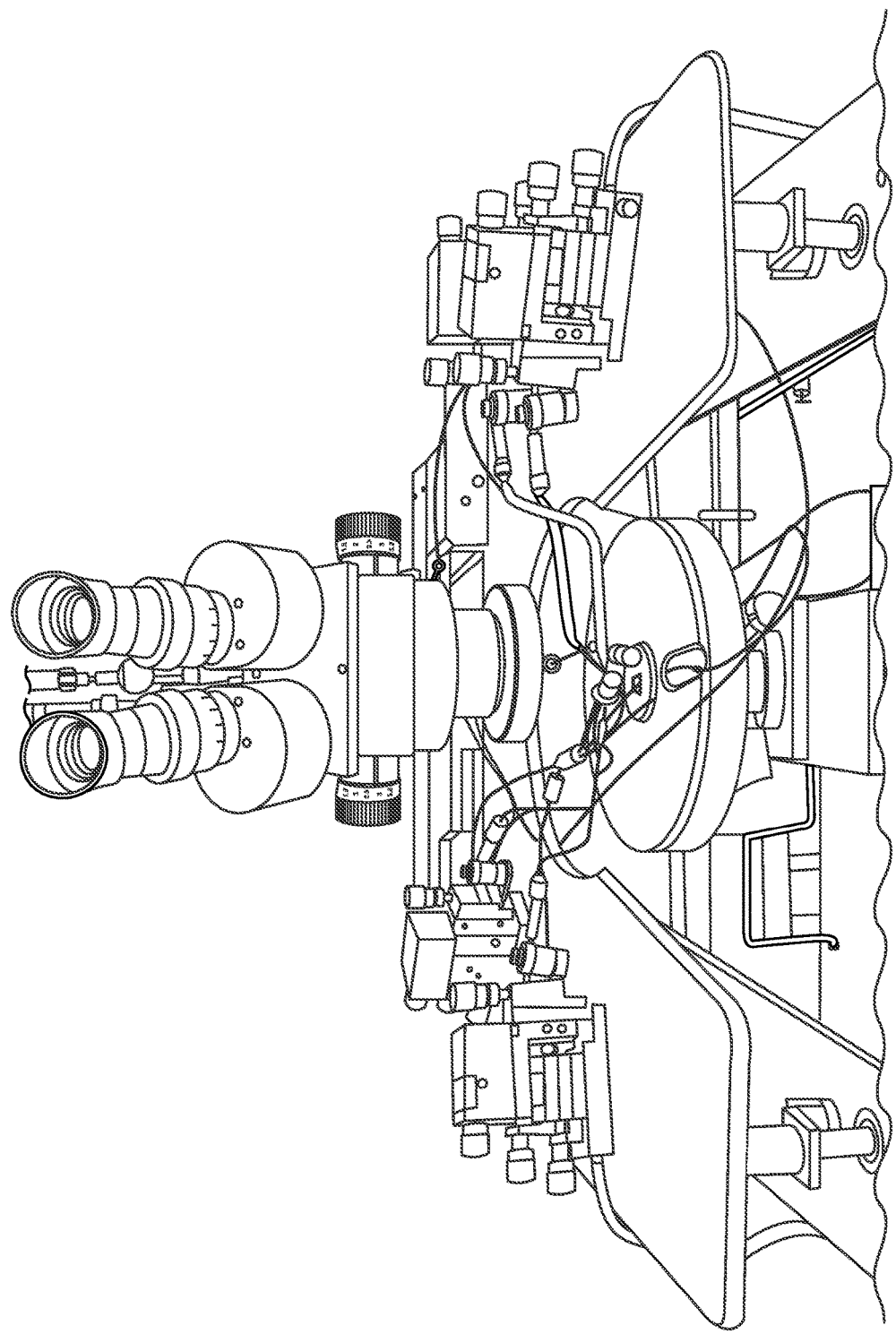
FIG. 8 shows a photo of the equipment used for testing the prototype graphene sensor.
Figure 9:
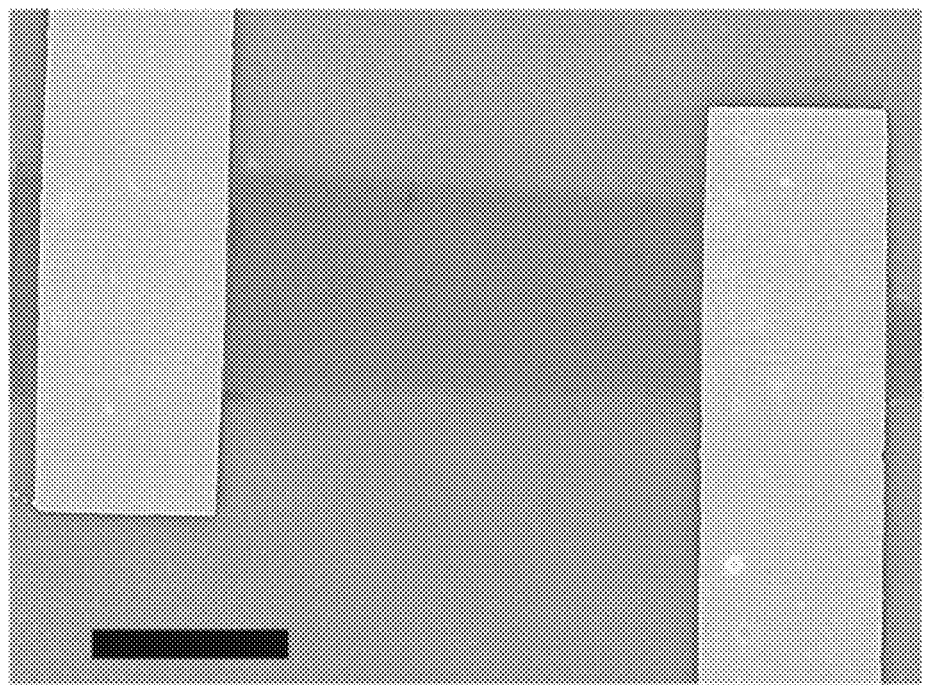
FIG. 9 shows an optical microscopy image of the prototype graphene sensor.

FIG. 8 shows a photo of the equipment used for testing the prototype graphene sensor. FIG. 9 shows an optical microscopy image of the prototype graphene sensor.

Figure 10:
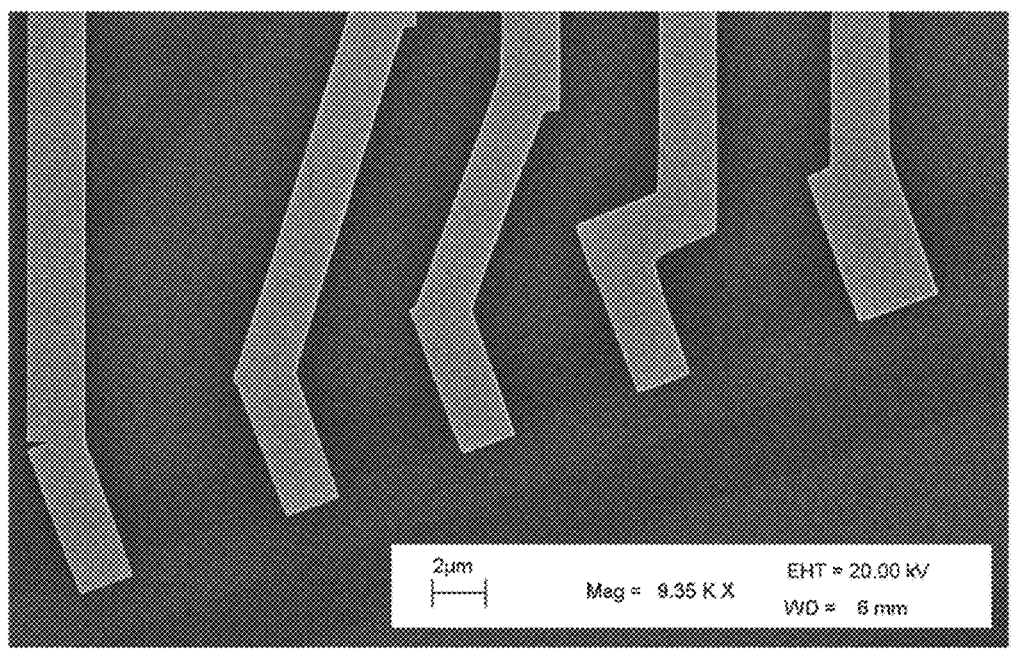
FIG. 10 shows a scanning electron microscopy image of the prototype graphene sensor array.

FIG. 10 shows a scanning electron microscopy image of the prototype graphene sensor array. In accordance with an exemplary embodiment, the graphene sensor array can be implemented on the same graphene ribbon with the metal electrode performing the role of the source and drain. The distance between different pairs of electrodes can vary to enable detection of various agents. For example, for large objects such as viruses or bacteria the source and drain distance have to be larger (from tens to hundreds micrometers or millimeters). The source, for example, drain distance for sensor elements for detection of gases and vapors can be small, for example from sub-micrometer to about ten micrometers. The graphene sensor array design can be extended to the whole wafer area with a set of graphene ribbons. Each ribbon can have multiple electrodes with different distances between the pairs of electrodes used as the source, for example, drain contacts.

When the word "about" is used in this specification in connection with a numerical value, it is intended that the associated numerical value include a tolerance of ±10% around the stated numerical value. Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features, which meet the strict definitions but also features, which fairly approximate the strict definitions.

The invention is not limited, however, to the embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents, which fall within the scope of the claims, are embraced by the claims.

What is claimed is:

1. A graphene sensor for selective sensing of vapors, gases and biological agents, the graphene sensor comprising:
   a substrate;
   a dielectric substrate on an upper layer of the substrate;
   a layer of graphene on an upper layer of the dielectric substrate;
   a source and drain contact on an upper surface of the layer of graphene;
   a pre-amplifier configured to amplify current fluctuations; and
   a low-pass and/or a high-pass filter configured to pass the amplified current fluctuations for analyzation.

2. The graphene sensor of claim 1, wherein the layer of graphene is single layer graphene (SLG).

3. The graphene sensor of claim 1, wherein the layer of graphene is a bilayer graphene (BLG).

4. The graphene sensor of claim 1, wherein the substrate is a p-typed highly-doped Si wafer.

5. The graphene sensor of claim 1, wherein the dielectric substrate is 300-nm thermally grown $SiO_2$.

6. The graphene sensor of claim 1, wherein the source and drain contact are Cr/Au.

7. The graphene sensor of claim 1, wherein the source and drain contact are Ti/Au.

8. The graphene sensor of claim 1, comprising:
a pair of Cr/Au contact pads.

9. The graphene sensor of claim 1, comprising:
a signal analyzer to measure a noise power spectrum.

10. The graphene sensor of claim 1, comprising:
an electrical circuit for a low frequency noise spectrum input.

11. The graphene sensor of claim 1, wherein the low-pass and/or the high-pass filter are configured to pass frequencies from 0.03 Hz to 100 KHz.

12. A graphene sensor for selective sensing of vapors, gases and biological agents, the graphene sensor comprising:
a substrate;
a dielectric substrate on an upper layer of the substrate;
one or more ribbons of graphene on an upper layer of the dielectric substrate;
a metal electrode acting as a source and drain contact;
a pre-amplifier configured to amplify current fluctuations; and
a low-pass and/or a high-pass filter configured to pass the amplified current fluctuations for analyzation.

13. The graphene sensor of claim 12, wherein the one or more graphene ribbons comprise a plurality of graphene ribbons.

14. The graphene sensor of claim 13, wherein each of the plurality of graphene ribbons has multiple electrodes.

15. The graphene sensor of claim 14, wherein the multiple electrodes have different distances between a pair of electrodes.

16. The graphene sensor of claim 12, comprising:
a signal analyzer to measure a noise power spectrum.

17. A method for selective detection of vapors, gases and biological objects with low frequency input as a sensing parameter using a graphene device, the method comprising:
exposing the graphene device to at least one vapor, gas, and/or biological object, the graphene device comprising a substrate, a dielectric substrate on an upper layer of the substrate, a layer of graphene on an upper layer of the dielectric substrate, and a source and drain contact on an upper surface of the layer of graphene, a pre-amplifier configured to amplify current fluctuations, and a low-pass and/or a high-pass filter configured to pass the amplified current fluctuations for analyzation; and
measuring a change in a noise spectra of the amplified current fluctuations of the graphene device.

18. The method of claim 17, comprising:
measuring the change in the noise spectra of the graphene device with a signal analyzer.

19. A method for selective detection of vapors, gases and biological objects with low frequency input as a sensing parameter using a graphene device, the method comprising:
exposing the graphene device to at least one vapor, gas, and/or biological object, the graphene device comprising a substrate, a dielectric substrate on an upper layer of the substrate, one or more ribbons of graphene on an upper layer of the dielectric substrate, a metal electrode acting as a source and drain contact, a pre-amplifier configured to amplify current fluctuations, and a low-pass and/or a high-pass filter configured to pass the amplified current fluctuations for analyzation; and
measuring a change in a noise spectra of the amplified current fluctuations of the graphene device.

20. The method of claim 19, comprising:
measuring the change in the noise spectra of the graphene device with a signal analyzer.

* * * * *